United States Patent
Roscoe et al.

(10) Patent No.: US 9,096,883 B2
(45) Date of Patent: Aug. 4, 2015

(54) MICROBIOLOGICAL SYSTEMS AND METHODS OF FLUID SAMPLE ANALYSIS

(75) Inventors: Stephen B. Roscoe, Woodbury, MN (US); Manjiri T. Kshirsagar, Woodbury, MN (US); Cynthia D. Zook, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 659 days.

(21) Appl. No.: 12/808,317

(22) PCT Filed: Dec. 18, 2008

(86) PCT No.: PCT/US2008/087399
§ 371 (c)(1), (2), (4) Date: Mar. 3, 2011

(87) PCT Pub. No.: WO2009/082667
PCT Pub. Date: Jul. 2, 2009

(65) Prior Publication Data
US 2011/0143334 A1 Jun. 16, 2011

Related U.S. Application Data

(60) Provisional application No. 61/016,265, filed on Dec. 21, 2007.

(51) Int. Cl.
*C12Q 1/24* (2006.01)
*C12Q 1/04* (2006.01)

(52) U.S. Cl.
CPC ... *C12Q 1/04* (2013.01); *C12Q 1/24* (2013.01)

(58) Field of Classification Search
None
See application file for complete search history.

(56) References Cited

U.S. PATENT DOCUMENTS

| | | | |
|---|---|---|---|
| 4,279,995 A | 7/1981 | Woods et al. | |
| 4,575,783 A | 3/1986 | Hammond | |
| 4,868,110 A | 9/1989 | DesRosier et al. | |
| 5,089,413 A | 2/1992 | Nelson et al. | |
| 5,118,750 A | 6/1992 | Silver et al. | |
| 5,194,374 A | 3/1993 | Rambach | |
| 5,232,838 A | 8/1993 | Nelson et al. | |
| 5,348,884 A | 9/1994 | Kulla | |
| 5,364,766 A | 11/1994 | Mach et al. | |
| 5,385,826 A | 1/1995 | Schell et al. | |
| 5,403,722 A | 4/1995 | Floeder et al. | |
| 5,434,056 A | 7/1995 | Monget et al. | |
| 5,443,963 A | 8/1995 | Lund | |
| 5,462,860 A | 10/1995 | Mach | |
| 5,601,998 A | 2/1997 | Mach et al. | |
| 5,629,170 A | 5/1997 | Mondello | |
| 5,635,367 A | 6/1997 | Lund | |
| 5,681,712 A * | 10/1997 | Nelson | 435/30 |
| 5,786,167 A | 7/1998 | Tuompo et al. | |
| 6,002,789 A | 12/1999 | Olsztyn et al. | |
| 6,022,682 A | 2/2000 | Mach et al. | |
| 6,251,624 B1 | 6/2001 | Matsumura et al. | |
| 6,331,429 B1 | 12/2001 | Ushiyama | |
| 6,368,817 B1 | 4/2002 | Perry et al. | |
| 6,565,749 B1 | 5/2003 | Hou et al. | |
| 6,596,532 B1 | 7/2003 | Hyman et al. | |
| 6,617,149 B2 | 9/2003 | Restaino | |
| 6,638,755 B1 | 10/2003 | Mizuochi et al. | |
| 6,756,225 B2 * | 6/2004 | Bedingham et al. | 435/305.1 |
| 7,150,977 B2 | 12/2006 | Restaino | |
| 7,298,885 B2 | 11/2007 | Green et al. | |
| 7,298,886 B2 | 11/2007 | Plumb et al. | |
| 7,351,548 B2 | 4/2008 | Rambach | |
| 2001/0041352 A1 | 11/2001 | Reilly et al. | |
| 2003/0088946 A1 | 5/2003 | Ferguson et al. | |
| 2003/0100104 A1 | 5/2003 | Jeffrey et al. | |
| 2004/0101954 A1 | 5/2004 | Graessle et al. | |
| 2004/0102903 A1 | 5/2004 | Graessle et al. | |
| 2005/0053266 A1 | 3/2005 | Plumb et al. | |
| 2006/0040400 A1 | 2/2006 | Mizutani et al. | |
| 2006/0257967 A1 | 11/2006 | Restaino | |
| 2007/0259393 A1 | 11/2007 | Restaino | |
| 2008/0096195 A1 | 4/2008 | Rambach | |

FOREIGN PATENT DOCUMENTS

| | | |
|---|---|---|
| EP | 1 494 358 | 12/1977 |
| EP | 0 398 703 | 11/1990 |
| EP | 0 454 046 | 10/1991 |
| JP | 08-336381 | 12/1996 |
| JP | 2001-321196 | 11/2001 |
| JP | 2004-57054 | 2/2004 |
| JP | 2006-230219 | 9/2006 |
| WO | WO 82-02563 | 8/1982 |
| WO | WO 92-07899 | 5/1992 |

(Continued)

OTHER PUBLICATIONS

Donofrio et al, "Evaluation of Four Membrane Filter Materials for Use with 3M™ Petrifilm™ *E. coli* Coliform Count Plates to Enumerate *Escherichia coli* in Water Samples" publication date unknown.*

3M Petrifilm™ *E.coli*/coliform Count Plates Instruction Manual (Carolina Teamed with Teachers, Carolina Biological Supply Company, 2000).*

Baumgartner, A. et al."Quantitative Analysis of *E. coli* in Water Comparison of ECD Agar and Petrifilm™", Mitt. Gebiete Lebensm. Hyg.; vol. 84 1993, pp. 382-387.

Buhler, H.P. et al.; "Microbiological Evaluation of Drinking water: Modified Application of the 3M Petrifilm-Systems under Field Conditions", Schweiz Z. Milit. Med., vol. 70, No. 1, 1993; pp. 9-12.

(Continued)

*Primary Examiner* — Patricia A Duffy

(57) ABSTRACT

Methods and systems for detecting the presence of a target microorganism in a liquid sample are provided. Methods comprise the steps of passing the liquid sample through a surface filter, placing the surface filter into contact with a culture device, incubating the culture device for a period of time and detecting the presence of a target microorganism. Methods may be used with an automated detection system.

2 Claims, 2 Drawing Sheets

(56) References Cited

FOREIGN PATENT DOCUMENTS

| WO | WO 96-06183 | 2/1996 |
|----|----|----|
| WO | WO 96-38533 | 12/1996 |
| WO | WO 98-06870 | 2/1998 |
| WO | WO 98-33069 | 7/1998 |
| WO | WO 99-18232 | 4/1999 |
| WO | WO 00-53721 | 9/2000 |
| WO | WO 01-14583 | 3/2001 |
| WO | WO 02-46354 | 6/2002 |
| WO | WO 2005-024047 | 3/2005 |
| WO | WO 2006-112709 | 10/2006 |
| WO | WO 2007-023186 | 3/2007 |
| WO | WO 2008-118400 | 10/2008 |
| WO | WO 2008-150779 | 12/2008 |
| WO | WO 2009-067498 | 5/2009 |
| WO | WO 2009-067503 | 5/2009 |
| WO | WO 2009-067513 | 5/2009 |
| WO | WO 2009-067518 | 5/2009 |
| WO | WO 2009-108229 | 9/2009 |
| WO | WO 2010-147918 | 12/2010 |
| WO | WO 2011-082305 | 7/2011 |

OTHER PUBLICATIONS

Ingham, C.J. et al. "Growth and Multiplexed Analysis of Microorganisms on a Subdivided, Highly Porous, Inorganic Chip Manufactured from Anapore", Applied and Environmental Microbiology, vol. 71, No. 12, 2005; pp. 8978-8981.

Sadler, P.W. et al.; "Synthesis and Absorption Spectra of Symmetrical Chloroindigos". J. Am. Chem. Soc., vol. 78, 1956; pp. 1251-1255.

Sambrook, J. et al.; Molecular Cloning—A Laboratory Manual, Third Edition, vol. 2, Cold Spring Harbor Laboratory Press, Cold Spring Harbor, NY, (2001), Title, copyright and Table of Contents 18 pages.

Schraft, H. et al.; "Enumeration of heterotrophs, fecal coliforms and *Escherichia coli* in water: comparison of 3M™ Petrifilm™ plates with standard plating procedures", Journal of Microbiological Methods, vol. 60, 2005; pp. 335-342.

Food and Drug Administration Bacteriological Analytical Manual ("BAM"), $8^{th}$ Ed., Revision A, (1998), AOAC International, Gaithersburg, MD, Title, copyright and Table of Contents 4 pages.

"Standard Methods for the Examination of Dairy Products", $17^{th}$ Edition, Edited by H. M. Wehr et al.; The American Public Health Association, Washington, D.C., 2004, Title, copyright and Table of Contents 6 pages.

"Standard Methods for the Examination of Water and Wastewater," $20^{th}$ Edition; Edited by L. S. Clesceri et al.; American Public Health Association; 1998, Title, copyright and Table of Contents 23 pages.

"AOAC Official Method 991.14 Coliform and *Escherichia coli* Counts in Foods—Dry Rehydratable Film (Petrifilm™ E.coli/ Coliform Count Plate™ and Petrifilm™ Coliform Count Plate™) Methods", Official Methods of Analysis of AOAC International, $18^{th}$ Edition, 2005, Current through Revision 4, 2011, AOAC International, Gaithersburg, MD, Title, copyright and method 3 pages.

ISO 9308-1. Water quality—Detection and enumeration of *Escherichia coli* and coliform bacteria—Part 1: Membrane filtration method, 2007, 24 pages.

Brochure entitled "3M Petrifilm™ Coliform Count Plate—Interpretation Guide"; #70-20084573-6 (1291.2) DPI; 1999; 6 pgs.

US 4,476,226, 10/1984, Hansen et al. (withdrawn)

* cited by examiner

MICROBIOLOGICAL SYSTEMS AND METHODS OF FLUID SAMPLE ANALYSIS

CROSS REFERENCE TO RELATED APPLICATIONS

This application claims the benefit of U.S. Provisional Application Ser. No. 61/016,265, filed Dec. 21, 2007.

BACKGROUND

The presence of coliform or other indicator bacteria is important evidence of food and water quality. The permitted amount of coliform bacteria found in drinking water or certain foods, such as dairy products, is regulated in many countries and/or municipalities. Coliforms include bacteria originating from nature, such as those found in soil. The coliform bacteria also include fecal coliforms, such as *Escherichia coli*. The presence of fecal coliforms in a sample is a primary indication of recent fecal contamination of the food or water, and of the possible presence of pathogenic organisms.

Methods for enumerating microbes in water samples can be found in, for example, the compendium "Standard Methods for the Examination of Water and Wastewater" (SMEWW), 21$^{st}$ Edition, which is a joint publication of the American Public Health Association, the American Water Works Association, and the Water Environment Federation. SMEWW describes a membrane filtration technique to obtain a direct count of microorganisms in water. Membrane filtration techniques are useful in monitoring the microbiological quality of samples from processes intended to produce drinking water, as well as samples from a variety of natural, unprocessed water sources.

Methods for enumerating microbes in food samples often vary according to the nature of the food and the types of organisms that are likely to be found in the samples. Several compendia of methods for testing food samples include "Standard Methods for the Examination of Dairy Products", 27$^{th}$ Edition, published by The American Public Health Association, Washington, D.C., and the Bacteriological Analytical Manual ("BAM"), published by the U.S. Food and Drug Administration, Washington, D.C. Solid foods are usually suspended in aqueous media and mixed and/or pulverized to obtain a liquid homogenate of the food material, which can be used in methods of quantitative microbial analysis.

Each of the aforementioned methods typically requires a highly skilled technician to observe and interpret the test results. There is a need for a simple, accurate method for determining the number of microorganisms in a liquid sample.

SUMMARY

In one embodiment, the present invention includes a method of detecting the presence of a target microorganism in a sample. The method can include providing a sample suspected of containing target microorganisms, a surface filter, and a culture device comprising culture medium. The method further can include collecting the target microorganisms on the filter, placing the surface filter into contact with the culture medium, incubating the culture device for a period of time, and detecting the presence of the target microorganism. The target microorganism optionally can be detected with an automated detection system.

In another embodiment, the present invention includes a method of detecting the presence of a target microorganism in a liquid sample. The method can include providing a liquid sample suspected of containing a target microorganism, a culture device comprising culture medium, and a filter which is substantially transparent when in contact with hydrated culture medium in the culture device. The method further can include collecting the target microorganisms on the filter, placing the filter into contact with the culture medium, incubating the culture device for a period of time, and detecting the presence of the target microorganism. The target microorganism optionally can be detected with an automated detection system.

In another embodiment, the present invention includes a method for detecting a gas-producing microorganism. The method can include providing a sample suspected of containing a gas-producing microorganism, a surface filter, and a flat film culture device containing culture medium comprising a fermentable nutrient. The method further can include collecting a gas-producing microorganism from the sample on the surface filter, placing the surface filter into contact with the culture medium, incubating the surface filter in contact with the culture medium for a period of time, and detecting the presence of a gas-producing microorganism. The target microorganism optionally can be detected with an automated detection system.

In another embodiment, the present invention includes a method for detecting a gas-producing microorganism. The method can include providing a sample suspected of containing a gas-producing microorganism, a culture device comprising culture medium containing a fermentable nutrient, a filter which is substantially transparent when in contact with hydrated culture medium in the culture device, and an automated detection system. The method further can include collecting a gas-producing microorganism from the sample on the filter, placing the filter into contact with the culture medium, incubating the surface filter in contact with the culture medium for a period of time, and detecting the presence of a gas-producing microorganism. The target microorganism optionally can be detected with an automated detection system.

The term "culture device" refers to a device that is used to propagate microorganisms under conditions that will permit at least one cell division to occur. Culture devices include a housing (e.g., a petri dish with a cover) to minimize the possibility of incidental contamination and a source of nutrients to support the growth of microorganisms.

The term "filter" refers to a relatively planar membrane filter, which is comprised of upper and lower major surfaces. Membrane filters are comprised of upper and lower major surfaces and of pores, flow paths, or passageways, through which fluids and particulates can pass from the upper surface to the lower surface of the filter. As used herein, the "upper major surface" refers to the major surface of the filter through which the fluid sample (e.g. a liquid or a gas with suspended particulates) enters the filter. The term "lower major surface" refers to major surface of the filter through which the filtrate exits the filter.

As used herein, "surface filter" or "surface-type filter" refers to a type of filter wherein the cross-sectional area at the opening of an individual passageway at the surface of the filter is generally about the same size as the cross-sectional area of that passageway at any other point within the filter. A surface filter excludes particles larger than the opening of individual passageways from entering or passing through the filter, thus the particles typically remain on the surface of the filter.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a liquid sample suspected of containing "a" target microorganism can be interpreted to mean that the liquid sample can include "one or more" target microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

DETAILED DESCRIPTION

The present invention relates to methods for the detection and/or enumeration of microorganisms in a liquid sample. The invention further relates to the use of membrane filters, in conjunction with culture devices, to detect and/or enumerate microorganisms in a liquid sample. Culture devices, such as 3M PETRIFILM plates (3M Company, St. Paul, Minn.) are sample-ready devices that can be used for the propagation and detection of microorganisms. Additionally, the PETRIFILM plates contain indicators that facilitate the detection and enumeration of certain target microorganisms.

Figure 1:
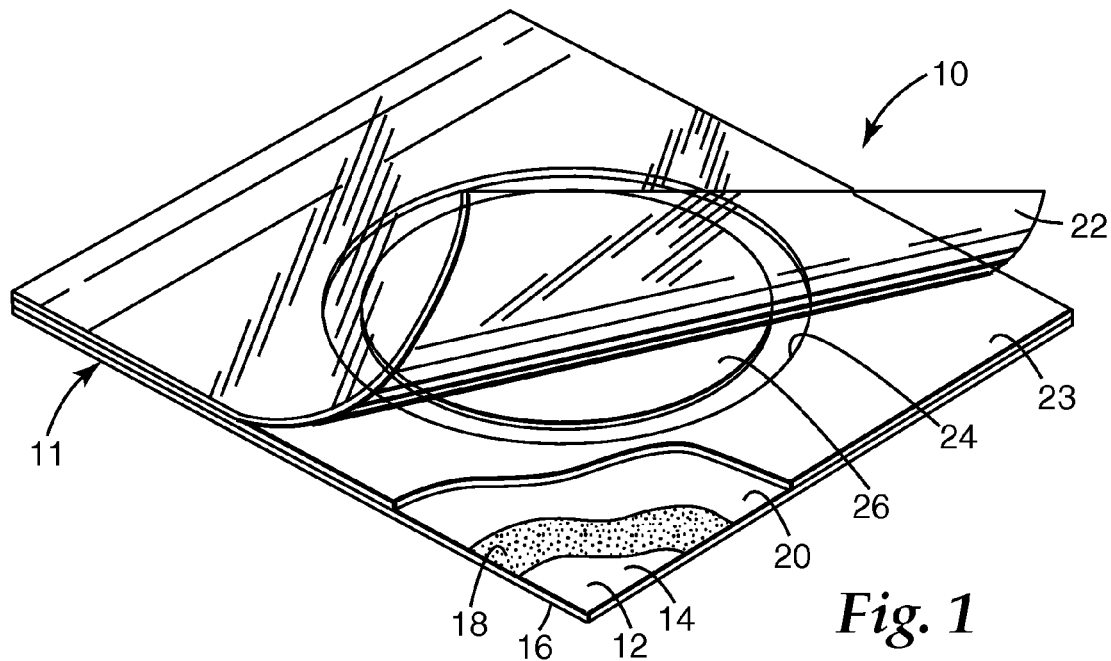
FIG. 1 is a perspective view of an opened flat film culture device comprising a spacer with an aperture with a filter membrane inserted therein, according to one embodiment of the present invention.
Figure 2:
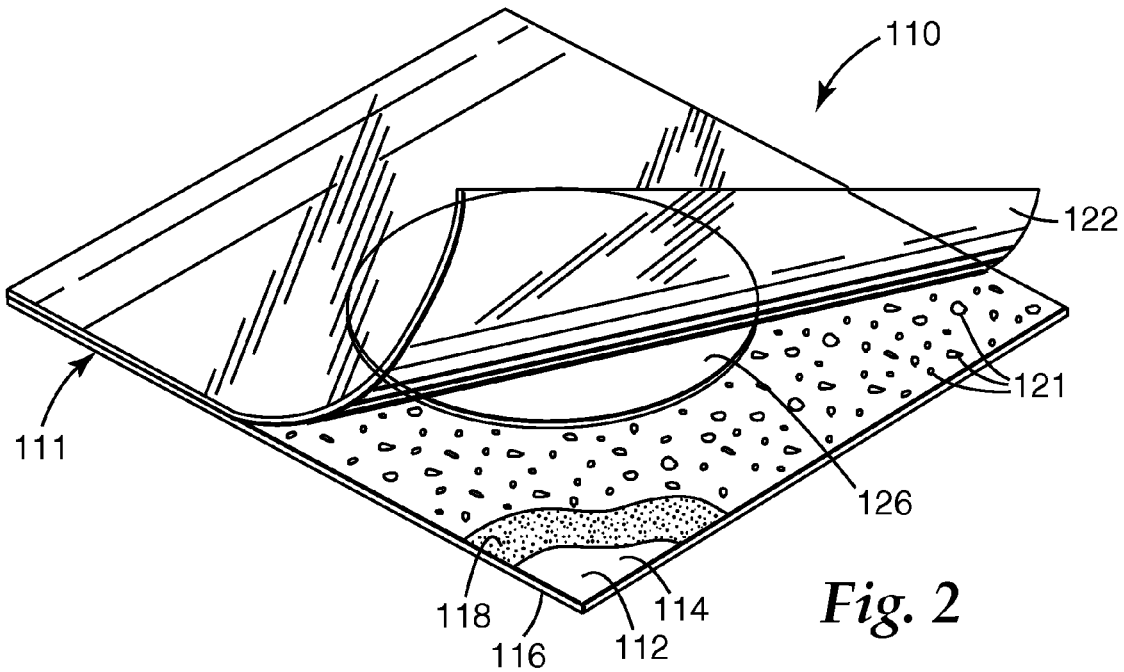
FIG. 2 is a perspective view of an opened flat film culture device with a filter membrane inserted therein, according to one embodiment of the present invention.

FIG. 1 shows a flat film culture device 10 which may be used in accordance with the present invention. Culture device 10 includes body member 11 comprising self-supporting substrate 12 having upper and lower surfaces 14 and 16, respectively. Substrate 12 is coated on its upper surface 14 with a layer of adhesive composition 18. Cold-water-reconstitutable dry medium 20, containing at least one ingredient selected from the group consisting of one or more gelling agents and one or more nutrients, is adhered in a thin, relatively uniform layer to the adhesive composition 18. Spacer 23 partially covers substrate 12 and the surface of dry medium 20 and contains aperture 24, which exposes a portion of dry medium 20. A cover sheet 22 overlays the spacer 23 and the aperture 24. If the cover sheet 22 is lifted to expose the dry medium 20, a membrane filter 26 through which a liquid sample has been passed can be placed onto the exposed dry medium 20 in the aperture 24. The membrane filter 26 can be placed onto the dry medium 20 in either orientation (i.e., with the upper major surface of the membrane filter 26 facing toward the dry medium 20 or with the upper major surface of the membrane filter 26 facing toward the cover sheet 22). After placing the membrane filter 26 onto the dry medium 20, a suitable volume of aqueous solvent (e.g., sterile water) can be deposited into the aperture 24 and a cover sheet 22 can be lowered onto the membrane filter 26 and/or the spacer 23. Cover sheet 22 may further comprise an adhesive layer and a dry medium layer, as shown in FIG. 2 of U.S. Pat. No. 5,089,413. Once hydrated with an aqueous solvent (not shown) which may comprise solutes, the layer of cold-water-reconstitutable dry medium 20 quickly forms a reconstituted medium (not shown), which in turn is capable of growing microorganisms present on the surface of a membrane filter 26. In an alternative embodiment, the dry medium 20 can be hydrated with the aqueous solvent, forming a reconstituted medium, prior to inserting the membrane filter 26 into the culture device.

FIG. 2 shows a flat film culture device 110 that may be used in accordance with the present invention. The culture device 110 includes body member 111 comprising self-supporting substrate 112 having upper and lower surfaces 114 and 116, respectively. Substrate 112 is coated on its upper surface 114 with a layer of adhesive composition 118. Cold-water-reconstitutable dry powder 121, containing at least one ingredient selected from the group consisting of one or more gelling agents and one or more nutrients, is adhered in a thin, relatively uniform layer to the adhesive composition 118. A cover sheet 122 overlays the dry powder 121. If the cover sheet 122 is lifted, a membrane filter 126 through which a liquid sample has been passed can be placed onto the dry powder 121. The membrane filter 126 can be placed onto the dry powder 121 in either orientation (i.e., with the upper major surface of the membrane filter 126 facing toward the dry powder 121 or with the upper major surface of the membrane filter 126 facing toward the cover sheet 122). After placing the membrane filter 126 onto the dry powder 121, a suitable volume of aqueous solvent (e.g., sterile water) can be deposited onto the membrane filter 126 and cover sheet 122 can be lowered onto the membrane filter 126. Once hydrated with an aqueous solvent (not shown), the layer of cold-water-reconstitutable dry powder 121 quickly forms a reconstituted medium (not shown), which in turn is capable of growing microorganisms present on the surface of a membrane filter 126. In an alternative embodiment, the dry powder 121 can be hydrated with the aqueous solvent, forming a reconstituted medium, prior to inserting the membrane filter 126 into the culture device.

Figure 3:
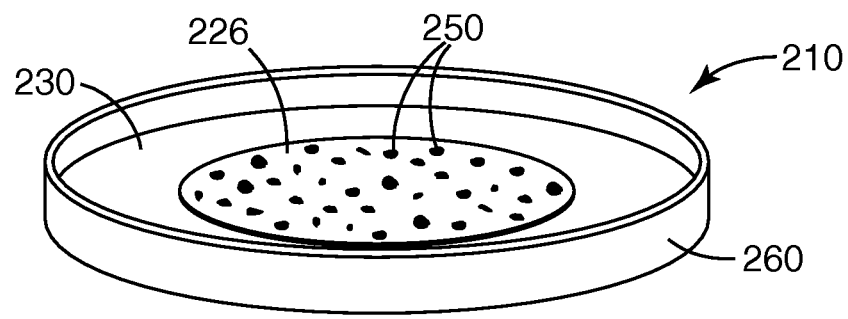
FIG. 3 is a perspective view of a petri dish containing semi-solid culture medium with a filter membrane disposed thereon, according to an embodiment of the present invention.

FIG. 3 shows an alternative culture device 210 that can be used according to the present invention. Culture device 210 is comprised of a vessel 260 containing semisolid culture medium 230. There are a number of suitable vessels 260 that are known in the art. Suitable vessels 260 include petri dishes, flasks, bottles, tubes, beakers, and the like. Preferably, the vessel is sterile or can be sterilized to prevent contamination of the sample or the culture medium 230. The vessel 260 may be covered (not shown) with a lid, a cap, or the like, to prevent contamination and/or to prevent desiccation of the sample or the culture medium 230. A membrane filter 226 through which a liquid sample has been passed can be placed onto the culture medium 230. The membrane filter 226 can be placed onto the culture medium 230 in either orientation (i.e., with the upper major surface of the membrane filter 226 facing toward the culture medium 230 or with the lower major surface of the membrane filter 226 facing toward the culture medium 230). FIG. 3 shows microbial colonies 250 that can be observed on membrane filter 226 after incubation under suitable conditions.

Figure 4:
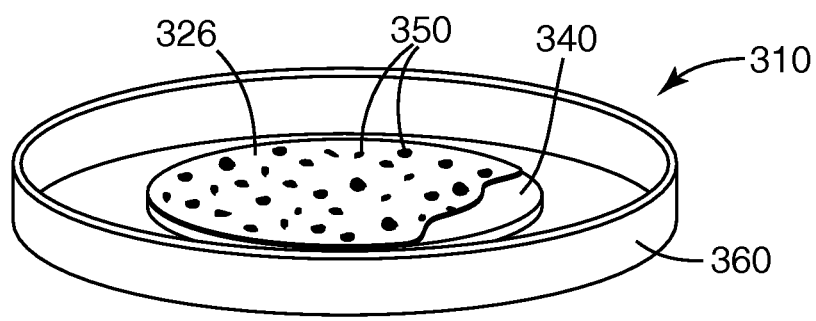
FIG. 4 is a perspective view of a petri dish containing porous support with a filter membrane disposed thereon, according to an embodiment of the present invention.

FIG. 4 shows a culture device 310 that can be used in accordance with the present invention. Culture device 310 is comprised of a vessel 360 and a filter support 340. There are a number of suitable vessels 360 that are known in the art. Suitable vessels 360 include petri dishes, flasks, bottles, tubes, beakers, and the like. Preferably, the vessel is sterile or can be sterilized to prevent contamination of the sample or the porous support 340. Preferably, the vessel 360 can be covered (not shown) with a lid, a cap, or the like, to prevent contamination and/or to prevent desiccation of the sample or the porous support 340. The porous support 340 can be made from materials capable of supporting a membrane filter 326 such that, when the porous support 340 is saturated with an aqueous solvent, the porous support 340 provides contact between at least a part of the lower surface of the membrane filter 326 and the aqueous solvent. In some embodiments, the porous support 340 provides contact between the entire lower surface of the membrane filter 326 and the aqueous solvent. The aqueous solvent may comprise a solution containing a nutrient to support the growth of a target microorganism and/or may comprise a solution containing a reagent to detect a target microorganism. Alternatively, the porous support may comprise a powder containing a nutrient to support the growth of a target microorganism and/or a powder containing a reagent to detect the presence of a target microorganism. A person of ordinary skill in the art is familiar with appropriate nutrients and reagents to grow and/or detect target microorganisms. Nonlimiting examples of suitable materials for a porous support 340 include cellulosic materials, such as filter paper; foams, such as polyurethane foams; hydrogels; sintered glass; and the like. After the liquid sample has been passed through the membrane filter 326, the membrane filter 326 can be placed onto the porous support 340 in either orientation. Preferably, the membrane filter 326 is placed onto the porous support 340 with the upper major surface of the membrane filter 326 facing toward the porous support.

Samples and Target Microorganisms

The sample used in the inventive methods can be liquid samples or solid samples that are suspended in a liquid medium. Preferably, solid sample can be treated either physically (e.g. homogenized) and/or chemically (e.g. by mixing with a surfactant) to suspend the target microorganisms in the liquid medium. Liquid samples may contain suspended solids, provided the concentration or size of the suspended solids does not prevent filtering the sample through a surface-type membrane filter. Liquid or suspended solid samples may be diluted in a suitable solvent (e.g., sterile water or buffer solution) prior to filtration.

Aqueous samples may be suitable for use in the inventive methods, provided that the aqueous samples do not degrade the membrane filter or leave a residue on the filter that would interfere with the detection of the target microorganisms (e.g., inhibit the growth of the microorganism). Nonaqueous samples also may be used, provided that the nonaqueous samples do not prevent the membrane filter from becoming transparent when placed in contact with the culture device, do not degrade the membrane filter, or do not leave a residue on the filter that would interfere with the detection of the target microorganisms (e.g., the residue does not interfere with the growth of the microorganism or interfere with an enzyme activity that can be used to detect the microorganism). Nonlimiting examples of liquid samples that may be suitable for use in the inventive methods include surface water, water for human or animal consumption, water for biopharmaceutical preparations, food or dairy products suspended in an aqueous solvent, beverages, fruit juice, process water, cooling water, circulating water, boiler water, boiler feed water, ground water, recreational water, treated water, and wastewater.

The inventive methods are suitable to detect or identify a variety of target microorganisms. The methods are suitable for target microorganisms that can be grown and/or propagated in a culture device. The target microorganism can be a bacterium, a yeast, a mold, or a virus. The methods may be used to detect aerobic or anaerobic bacteria. Exemplary target microorganisms include species from the genera *Enterobacter, Citrobacter, Serratia, Yersinia, Escherichia, Hafnia, Salmonella, Campylobacter, Listeria, Staphylococcus, Enterococcus,* and *Thiospirillum*; species from the family Enterobacteriaceae; coliforms; fecal coliforms; fecal *Streptococcus* species; *Escherichia coli; Hafnia alvei; Enterobacter amnigenus; Cylospora* or *Cryptosporidium* species; rotavirus; and hepatitis A virus.

Membrane Filters and Filtration Units

The target microorganisms can be collected on a membrane filter by transferring a liquid or solid sample onto the surface of the filter or by filtering a liquid sample through the membrane filter. After collecting the sample on the membrane filter, the filter can be transferred to a culture device. Membrane filters can be surface-type microporous membrane filters which are not inhibitory to the growth or metabolic activity of the target microorganisms. The membrane filters may be made from, for example, ceramic aluminum oxide, track-etched polycarbonate, or track-etched polyester. Suitable membrane filters also include filters which are substantially transparent when in contact with hydrated culture medium, such as hydrated culture medium in a culture device. As used herein, a "substantially transparent" membrane filter refers to a membrane filter that does not significantly distort or impair the observation or imaging of indicia of microbial growth (e.g., a colony, a pH indicator, a gas bubble, a product or intermediate of an enzyme reaction) in a culture device. Nonlimiting examples of suitable membrane filters include ceramic membrane filters sold by Whatman Inc. (Florham Park, N.J.) under the trade name ANOPORE, which have a thickness of about 60 µm, a porosity of about 25-50%, and a refractive index of about 1.6 and track-etched polycarbonate filters sold by Whatman Inc. under the trade name NUCLEOPORE, which have a thickness of about 10-20 µm, a porosity of about 15%, and a refractive index of about 1.6.

Pore sizes of the membrane filter generally are chosen so that the target microorganisms will not pass though the pores, thereby insuring that substantially all target microorganisms in the sample are collected on the filter. Typical bacteria are about 0.5 to 5.0 µm in length. Certain smaller bacteria, such as *Mycoplasma*, are approximately 0.3 µm in diameter. Yeast cells are generally larger than bacteria. Typical yeast cells are approximately 3-4 µm in diameter, although some are as large as about 40 µm in diameter. Molds may exist as single cells, spores, or filamentous hyphae. Although typically larger than bacteria, the average size of mold cells varies by species. Viruses are typically smaller than bacteria. For example, rotaviruses are about 0.07 µm in diameter, hepatitis A viruses are about 0.027 µm in diameter, caliciviruses (e.g. Noroviruses) are about 0.027-0.040 µm in diameter, picornaviruses (e.g. poliovirus) are about 0.03 μm in diameter, and enteric adenoviruses are about 0.07 μm in diameter. Accordingly, the selection of a membrane filter with a suitable pore size may depend upon the target microorganism. For example, a membrane filter with a pore size of 1.0 μm or less, 0.8 μm or less, 0.6 μm or less, 0.4 μm or less, 0.2 μm or less, 0.1 μm or less, 0.05 μm or less, 0.03 μm or less, 0.02 μm or less, or 0.01 μm or less may be suitable to capture and detect target bacteria. For the capture and detection of target yeast or mold, a membrane filter with pore size of 12 μm or less, 8 μm or less, 5 μm or less, 3 μm or less, 2 μm or less, 1 μm or less, 0.8 μm or less, 0.6 μm or less, 0.4 μm or less, 0.2 μm or less, or 0.1 μm or less may be suitable. For the capture and detection of target viruses, a membrane filter with a pore size of 0.05 μm or less, 0.03 μm or less, 0.02 μm or less, or 0.01 μm or less may be suitable.

Membrane filters may be prepared manually from suitable filtration media or, alternatively, may be purchased in pre-cut sizes and shapes. The size and shape of the membrane filter can be chosen based upon the sample volume and the expected load of particulate material in the sample. In general, membrane filters with larger surface areas will allow for higher filtration rates than membrane filters with smaller surface areas. Circular membrane filters, having a diameter of 13 mm, 25 mm, or 47 mm, are readily available from a number of commercial sources and are particularly suitable for use with corresponding filtration devices. Membrane filters may be used in combination with other filtration media (e.g., a prefilter, to trap larger debris in the sample) or other membrane filters. For example, membrane filters may be stacked in order of decreasing pore size in order to separate larger microorganisms (e.g., yeast and mold) from smaller microorganisms (e.g., bacteria or viruses), allowing the membrane filters to be analyzed separately to detect different microorganisms.

The membrane filter can be used in conjunction with a filtration unit. The filtration unit can be used to hold the membrane filter while the liquid sample is passed through the membrane filter. After the liquid sample has passed through the membrane filter, the membrane filter can be removed from the filtration unit and transferred to a culture device. Preferred filtration units include those that are configured for easy removal of the membrane filter and placement of the membrane filter into a culture device.

The filtration device can be designed for attachment to or use with a syringe, such as the filter holders sold by Millipore Corporation under the trade name SWINNEX. Alternatively, for larger volumes, the filtration device can be designed for attachment to a flask. Preferably, the membrane filter and filtration device may be sterilized before passing a sample through the filter.

Exemplary systems in which the membrane filters and methods disclosed herein could be incorporated include those described in U.S. Patent Application No. 60/941,145, filed on May 31, 2007, and entitled "Devices and Processes for Collecting and Concentrating Samples for Microbiological Analysis"; U.S. Patent Application No. 60/989,180, filed on Nov. 20, 2007, and entitled "System and Method for Preparing and Analyzing Samples"; U.S. Patent Application No. 60/989,175, filed on Nov. 20, 2007, and entitled "System and Method for Preparing and Delivering Samples"; U.S. Patent Application No. 60/989,170, filed on Nov. 20, 2007, and entitled "System and Method for Preparing and Collecting Samples"; and U.S. Patent Application No. 60/989,332, filed on Nov. 20, 2007, and entitled "System and Method for Environmental Sampling".

Culture Devices

A variety of culture devices can be used in the inventive methods. In some embodiments, the culture devices can detect the presence of bacteria. In alternative embodiments, the culture devices can detect the presence of yeast and/or mold. In certain embodiments, the culture devices can detect the presence of viruses.

In some embodiments that are used to detect bacteria, yeast or mold, the culture devices can include a pre-formed hydrogel matrix (e.g., agar, agarose, calcium pectinate) comprising nutrients to support the growth of a target microorganism and, optionally, at least one indicator to facilitate the detection of the target microorganism. In some embodiments, the hydrogel further comprises at least one selective agent (such as a salt, a surfactant, or an antibiotic) to provide an environment that favors the growth or detection of the target microorganisms over nontarget microorganisms that may be present in the sample. The pre-formed hydrogel matrix can be placed into any suitable container, such as a petri dish, beaker, or flask. Preferably, the hydrogel and the container can be sterilized before the membrane filter is placed in contact with the hydrogel.

In other embodiments, the culture devices can include dry, rehydratable culture devices comprising nutrients to support the growth of a target microorganism and, optionally, at least one indicator to facilitate the detection of the target microorganism. Nonlimiting examples of such devices are described in U.S. Pat. Nos. 4,476,226; 5,089,413; 5,232,838; 6,331,429; and 6,638,755. Dry rehydratable culture devices can include gelling agents. Suitable gelling agents include cold water soluble natural and synthetic gelling agents. Nonlimiting examples of such gelling agents include guar gum, xanthan gum, hydroxyethyl cellulose, carboxymethyl cellulose, polyacrylamide, locust bean gum, algin, and combinations of two or more of the foregoing. Such devices can also include nutrients to support the growth or metabolism of microorganisms. Nonlimiting examples of nutrients that support the growth of a variety of microorganisms include peptones, yeast extract, glucose, and the like. Specific nutrients or combinations of nutrients required for growing and/or identifying certain organisms or groups of organisms are known in the art. In some embodiments, the dry rehydratable culture devices further comprise at least one selective agent (such as a salt, a surfactant, or an antibiotic) to provide an environment that favors the growth or detection of the target microorganisms over nontarget microorganisms that may be present in the sample.

In other embodiments, culture devices can include a porous support in fluid communication with an aqueous mixture comprising nutrients to support the growth of a target microorganism and, optionally, at least one indicator to facilitate the detection of the target microorganism. In some embodiments, the aqueous mixture further comprises at least one selective agent (such as a salt, a surfactant, or an antibiotic) to provide an environment that favors the growth or detection of the target microorganisms over nontarget microorganisms that may be present in the sample.

It is preferable that the porous support not contain materials which could be transported through an aqueous solvent and prevent the detection of the target microorganisms. Porous supports can be one of a variety of physical forms such as, for example, a fabric, a nonwoven, a gel, a foam, a mesh, a scrim, a frit, a microreplicated film, or the like. Certain porous supports are constructed from hydrophilic materials, such as filter paper or glass fiber filter. Alternatively, the support may be constructed from a hydrophobic material which has been treated to render the material hydrophilic or the hydrophobic material may be capable of transporting an aqueous solvent or solution by capillary action, for example.

The porous support can be placed into any suitable container, such as a petri dish, beaker, or flask. Preferably, the porous support and the container can be sterilized before the membrane filter is placed in contact with the porous support.

In certain embodiments, the culture device includes a housing with a host cell line contained therein. Certain viruses can be detected in a culture device by observing the cytopathic effect (CPE) that they cause when the virus particles infect cultured cell lines (tissue culture). Tissue culture techniques and their corresponding culture devices are known in the art. In these embodiments, a membrane filter through which a liquid sample has been passed may be transferred into a culture device containing a cell line. Alternatively, the viruses may be washed from the filter into a small volume of sterile water, buffer, or tissue culture medium and the resulting suspension can be added to the culture device. After a suitable period of incubation, the tissue culture can be observed for indications of CPE such as, for example, plaque formation. Plaques can be observed either visually or with the assistance of microscopes and/or imaging systems. Visual detection of plaques may be improved using stains such as crystal violet or immunoreagents such as, for example, fluorescent-labeled antibodies.

Sample Preparation Systems

Surface filters, filtration units, and culture devices can be combined with packaging material and sold as a sample preparation system (kit) for detecting microorganisms in a sample. For example, the sample preparation systems may comprise two or more components (e.g., a surface filter and a culture device) or three or more components (e.g., a surface filter, a filtration unit, and a culture device) packaged together. In certain embodiments, the filtration unit can be configured for the removal of the surface filter.

The sample preparation systems may further comprise sampling and testing accessories, such as a sample suspending medium (e.g., water, buffer, growth medium), a reagent (e.g., a dye, an indicator, an enzyme, an enzyme substrate, a lysing agent, a reagent to facilitate elution), a pipette, a label, forceps, a sample carrier, and/or a glove. In certain embodiments, the individual components of the sample preparation system can be sterilized. In certain embodiments, the components of the sample preparation system can be in individually-wrapped primary packaging.

Automated Detection Systems

Automated systems for counting microbial colonies in culture devices are known in the art. Such automated systems generally comprise an imaging system, an image analysis algorithm to determine a colony count, and a data management system to display and, optionally, store and manipulate the colony count data and images. An exemplary system for counting colonies on agar plates is sold by Synbiosis (Cambridge, UK) under the trade name PROTOCOL and in U.S. Pat. No. 6,002,789. Systems for counting colonies on PETRIFILM plates are described in U.S. Pat. Nos. 5,403,722; 7,298,885; and 7,298,886.

Typically, automated systems for counting microbial colonies detect the presence of target microorganisms by the ability of the colonies, or metabolites derived therefrom, either to absorb, reflect, emit or scatter light. Thus, the colonies can be detected optically by means such as, for example, colorimetically, fluorometrically, or lumimetrically (e.g. chemiluminescence or bioluminescence).

In certain tests, such as tests for coliform bacteria, it is desirable to determine whether the microorganisms produce gas (i.e., carbon dioxide) from lactose sugar. 3M PETRIFILM Coliform Count plates and *E. coli* Count plates incorporate lactose into the nutrient growth medium. In these tests, a coliform colony may be tentatively identified by a color change of a pH indicator in the growth medium. The pH change indicates that the colony may have produced acid end products from lactose and the colony is presumed to be a coliform colony. The presumed coliform colony may be confirmed as a coliform microorganism by observing the presence of one or more gas bubbles proximate the colony. The gas bubbles may be observed optically, either by visual means or by an automated system, such as the automated colony counting system described in U.S. Pat. No. 7,298,886. Flat film culture devices such as PETRIFILM *E. coli*/Coliform Count plates which, when hydrated and closed comprise a semi-solid growth medium in continuous contact with a self-supporting substrate on one side of the growth medium and a cover sheet on the other side of the growth medium (see FIGS. 1 and 2), are particularly suitable for trapping the gas bubbles produced by a lactose-fermenting coliform microorganism.

Confirmatory Identification Tests

Some culture devices of the present disclosure provide means, such as selective and/or differential reagents, for unambiguously identifying a microorganism present in the culture device. Other culture devices can provide a provisional identification of a microorganism present in the culture device. When such a provisional identification is made, occasionally it is desirable to confirm the identity of the microorganism by performing additional tests. The methods of the present disclosure provide for confirmatory tests.

After the culture device has been incubated and the presence of an organism has been observed (either visually or by an automated detection system), the target organisms may be removed from the culture device for further analysis or, in the instance of certain genetic or immunological tests, the analysis may be performed in the culture device (i.e., in situ). Further analysis may include chemical analyses (e.g., chromatography, spectroscopy, spectrometry), genetic analysis (e.g., hybridization, nucleic acid amplification), and immunological analysis (e.g., ELISA, immunochromatography, agglutination, radial immunoassay).

The analytical methods may be performed using the entire sample in the culture device by, for example, removing or extracting the microorganisms or components thereof from the entire membrane filter and culture media. Alternatively, smaller regions of the culture device or individual colonies may be isolated and/or extracted to perform the analytical methods. In some embodiments, a nitrocellulose or nylon membrane may be used to "lift" the microorganisms or components thereof and subsequently perform genetic, biochemical, or immunological tests. Specific analytical methods can be found in Molecular Cloning, A Laboratory Manual, $3^{rd}$ Edition (Cold Spring Harbor Laboratory Press, Cold Spring Harbor, N.Y.), which is incorporated herein by reference in its entirety.

EXAMPLES

Example 1

Visual Detection of Coliform Bacteria in Petrifilm *E. Coli*/Coliform Count Plates Petrifilm *E. coli*/Coliform Count (EC) Plates were obtained from 3M Company (St. Paul, Minn.). Mixed cellulose ester (MCE) membrane filters (47 mm diameter, 0.45 μm nominal pore size) were obtained from Millipore Corporation (Billerica, Mass.). Alumina matrix ceramic membrane filters (47 mm diameter, 0.2 µm nominal pore size) were obtained from Whatman (Florham Park, N.J.). *Enterobacter amnigenus* ATCC 51818 were obtained from the American Type Culture Collection (Manassas, Va.).

An overnight bacterial culture was grown in trypticase soy broth at 35° C. The overnight culture was diluted in 1.5 liters of untreated (e.g., water was not chlorinated, fluorinated, or softened) well water to a final concentration of approximately 0.5 to 1.0 colony-forming units per milliliter (CFU/mL). A 100 milliliter volume of the diluted culture was filtered through a membrane filter in a sterile filtration apparatus (Microfil V; Millipore Corporation, Billerica, Mass.). Using sterile forceps, the membrane was aseptically removed from the filtration apparatus and was placed onto the dry, circular media in a Petrifilm EC plate. One milliliter of sterile Butterfield's phosphate diluent was dispensed onto the membrane and the Petrifilm plate was closed and the diluent was distributed evenly across the plate according to the manufacturer's instructions. This step was performed with care to avoid the introduction of air bubbles into the plate during inoculation. Plates were incubated at 35° C. for 24±2 hours. Plates were counted manually according to the manufacturer's instructions. The results are shown in Table 1.

TABLE 1

Visual detection in Petrifilm plates of *Enterobacter amnigenus* on membrane filters.

| | Filter Type | |
|---|---|---|
| | Mixed Cellulose Ester | Ceramic |
| Colony Count | 59 | 82 |
| Colony Appearance | Small (<1 mm diameter), pale red, irregular-shaped colonies with diffuse margins | Small (ca. 1 mm diameter), dark red, circular colonies with well-defined margins and proximate gas bubbles. |

Example 2

Automated Detection of Coliform Bacteria in Petrifilm *E. Coli*/Coliform Count Plates An overnight culture of *Enterobacter amnigenus* was grown, diluted, and filtered as described in Example 1. The filters were placed into Petrifilm EC plates and were incubated as described in Example 1. The incubated plates were placed into a Petrifilm Plate Reader (3M Company, St. Paul, Minn.) and the number of coliform colonies was determined by the reader according to the manufacturer's instructions. The results are shown in Table 2.

TABLE 2

Automated detection in Petrifilm plates of *Enterobacter amnigenus* colonies on membrane filters.

| | Filter Type | |
|---|---|---|
| Colony Count | Mixed Cellulose Ester | Ceramic |
| Coliform count | 1 | 4 |
| Total count | 1 | 51 |

The plate reader detected only one colony on the MCE filter membrane. That colony was associated with a gas bubble and, therefore was counted as a coliform. Visual inspection of the plate showed that there were at least several dozen small, diffuse, red colonies that were not detected by the plate reader. In contrast, the plate reader detected fifty-one colonies on the ceramic filter membrane. Of those colonies, the reader detected four that were associated with a gas bubble.

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

Example 3

Automated Detection and Identification of a Mixed Suspension of Bacteria Using Petrifilm *E. Coli*/Coliform Count Plates Bacterial cultures were prepared as described in Example 1. The bacteria used in this example were *Hafnia alvei* ATCC 51815 (a species of coliform bacteria) and *Escherichia coli* ATCC 11229, both obtained from the American Type Culture Collection. The cultures were diluted as described in Example 1 and mixed to obtain a suspension of approximately 50-100 CFU of each organism per 100 milliliters of water. The 100 mL suspension was filtered and placed into a Petrifilm *E. coli*/Coliform Count Plate, as described in Example 1. The plates were incubated for 24 hours at 35° C. The incubated plates were passed through a Petrifilm Plate Reader and the images were analyzed for the presence and type of colonies in each plate. The data are presented in Table 3. Coliform and *E. coli* colonies were detected by the unmodified plate reader scanner and software system in the experiment using a ceramic membrane filter. Some blue colonies were growing on the MCE membrane filter were not recognized and counted by the automated reader.

TABLE 3

Plate reader colony counts from mixed cultures grown in Petrifilm *E. coli*/Coliform Count Plates. In this test, a typical colony of *Hafnia alvei* should appear as a red colony with a gas bubble and a typical colony of *Escherichia coli* should appear as a blue colony with a gas bubble. The last column shows the number of colonies that were clearly visible on the plate and the image of the plate, but were not recognized and counted by the image analysis software of the automated reader.

| | Colony-Forming Units | | | | |
|---|---|---|---|---|---|
| Membrane Type | blue with gas | blue without gas | red with gas | red without gas | Not counted by reader |
| MCE | 0 | 67 | 0 | 0 | 9 |
| Ceramic | 7 | 20 | 14 | 17 | 0 |

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

What is claimed is:

1. A method for detecting a gas-producing microorganism, comprising the steps of:

providing an automated detection system, a sample suspected of containing a gas-producing microorganism; a flat film culture device comprising a cover sheet that optionally includes a dry medium layer adhered thereto, a self-supporting substrate having a cold-water-reconstitutable dry medium adhered thereto, and a culture medium containing a fermentable nutrient; and a membrane filter which is substantially transparent when in contact with a hydrated culture medium in the culture device, the filter having a first major surface and a second major surface opposite the first major surface;

collecting a gas-producing microorganism from the sample onto the first major surface of the filter;

placing at least one major surface of the filter with the microorganisms collected thereon into contact with the reconstitutable dry medium;

hydrating the reconstitutable dry medium and the optional dry medium layer, if present, with a predetermined volume of aqueous liquid before or after placing the filter into contact with the dry medium in order to form a semi-solid growth medium;

closing the culture device to bring the cover sheet or the optional medium layer, if present, into contact with a major surface of the filter opposite the at least one major surface of the filter;

incubating the closed culture device for a period of time; and detecting the presence of a gas-producing microorganism;

wherein detecting the presence of the gas-producing microorganism comprises detecting the gas-producing microorganism with the automated detection system;

wherein detecting the presence of the gas-producing microorganism comprises detecting a colony;

wherein the colony is detected optically; and wherein detecting the presence of the gas-producing microorganism further comprises detecting a gas bubble proximate to the colony.

2. The method of claim 1 wherein the gas bubble is detected optically.

* * * * *